United States Patent
Lemaire et al.

(10) Patent No.: US 7,318,899 B2
(45) Date of Patent: Jan. 15, 2008

(54) METHOD OF SEPARATING ISOTOPES

(75) Inventors: Marc Lemaire, Villeurbanne (FR); Jacques Foos, Orsay (FR); Alain Guy, Pontcarre (FR); Frédéric Chitry, Villeurbanne (FR); Stéphane Pellet-Rostaing, Villeurbanne (FR); Olivier Vigneau, Lyons (FR)

(73) Assignee: Framatome Anp, Courbevoie (FR)

( * ) Notice: Subject to any disclaimer, the term of this patent is extended or adjusted under 35 U.S.C. 154(b) by 257 days.

(21) Appl. No.: 10/250,833

(22) PCT Filed: Jan. 5, 2001

(86) PCT No.: PCT/FR01/00037

§ 371 (c)(1),
(2), (4) Date: Oct. 29, 2003

(87) PCT Pub. No.: WO02/053269

PCT Pub. Date: Jul. 11, 2002

(65) Prior Publication Data

US 2004/0081604 A1    Apr. 29, 2004

(51) Int. Cl.
B01D 61/00 (2006.01)
B01D 61/02 (2006.01)
C02F 1/44 (2006.01)
C01G 56/00 (2006.01)
C02B 3/00 (2006.01)
C02F 60/02 (2006.01)

(52) U.S. Cl. .............. 210/652; 210/651; 210/634; 210/638; 210/639; 423/1; 423/2; 423/3; 423/21.1; 423/DIG. 7

(58) Field of Classification Search ........ 210/651–652, 210/634, 638, 639; 423/21.5, 9–11, 40, 24, 423/42, DIG. 7, 1–3, 21.1; 562/433
See application file for complete search history.

(56) References Cited

U.S. PATENT DOCUMENTS

| 2,835,687 | A |   | 5/1958 | Clewett et al. |
|---|---|---|---|---|
| 3,953,568 | A |   | 4/1976 | Seko et al. |
| 4,600,566 | A |   | 7/1986 | Fujine et al. |
| 5,110,566 | A | * | 5/1992 | Snyder et al. ............... 423/70 |
| 5,332,531 | A | * | 7/1994 | Horwitz et al. .............. 588/20 |
| 5,342,604 | A | * | 8/1994 | Wilson et al. ............ 424/1.65 |
| 5,618,433 | A | * | 4/1997 | Tarbet et al. ............... 210/634 |
| 5,766,478 | A | * | 6/1998 | Smith et al. ............... 210/638 |
| 6,214,301 | B1 | * | 4/2001 | Taylor et al. .................. 423/2 |
| 6,245,305 | B1 | * | 6/2001 | Bray et al. ..................... 423/2 |
| 6,335,420 | B1 | * | 1/2002 | Bruening et al. ........... 528/266 |
| 6,506,706 | B1 | * | 1/2003 | Bruening et al. ........... 502/401 |
| 6,623,644 | B2 | * | 9/2003 | Bruening et al. ........... 210/660 |
| 6,843,917 | B1 | * | 1/2005 | Guy et al. ................... 210/638 |

FOREIGN PATENT DOCUMENTS

| EP | 0 142 126 | 5/1985 |
|---|---|---|
| EP | 173484 | 3/1986 |
| FR | 881 316 | 4/1943 |
| FR | 1 583 034 | 10/1969 |
| FR | 2 214 509 | 8/1974 |
| FR | 2 600 264 | 5/1999 |
| WO | 92 006 75 | 12/1992 |
| WO | 96 001 23 | 8/1995 |
| WO | 96 001 24 | 11/1995 |

OTHER PUBLICATIONS

Whitworth T M et al: "Isotopic Fractionation and Overall Permeation of Lithium by a Thin-Film Composite Polyamide Reverse Osmosis Membrane" Journal of Membrane Science, Elsevier Scientific Publ. Company. Amsterdam, NL vol. 88 No. 2/3, Mar. 16, 1994, pp. 231-241. XP000488346 ISSN: 0376-7388.

* cited by examiner

Primary Examiner—Ana Fortuna
(74) Attorney, Agent, or Firm—Kenyon & Kenyon LLP

(57) ABSTRACT

A process in which isotopes of the same element belonging to the alkaline earth metals, transition elements and heavy metals having an atomic mass of less than 209, in particular lanthanide metals, are separated in an aqueous medium by treating an aqueous medium.

33 Claims, No Drawings

METHOD OF SEPARATING ISOTOPES

FIELD OF THE INVENTION

The invention relates to the separation of isotopes of alkaline earth metals, of transition elements and of heavy metals having an atomic mass of less than 209. It relates more particularly to the separation of the isotopes of rare earth metals or lanthanide metals. The invention thus relates to a process which allows separation of isotopes of these elements from one another.

BACKGROUND INFORMATION

Some isotopes of lanthanide metals are used as neutron poison or neutron absorber in nuclear reactors. This is the case in particular with gadolinium (Gd) and erbium (Er). Not all gadolinium isotopes (152, 154, 155, 156, 157, 158, 160) and erbium isotopes (162, 164, 166, 167, 168, 170) are equally advantageous and manufacturers are looking to isolate the most favorable isotopes. The 155 and 157 isotopes of gadolinium and the 167 isotope of erbium are the isotopes having the best neutron absorption capacities and are the isotopes of choice as products which absorb neutrons in fuel elements for nuclear power stations.

For further information on the isotopes of lanthanide metals, see Handbook of Chemistry and Physics, 73rd edition, 1992-1993.

The separation of the isotopes of the same element is one of the most difficult technical problems to solve, whatever the scale of separation chosen. It increases in difficulty as the difference in relative mass between the isotopes decreases, e.g. between 1 and 2% for lanthanide metals.

The separation of the isotopes of elements such as Ca or Na in the liquid phase (aqueous or organic phase) using complexing agents was carried out for the first time by the teams of Jepson and DeWitt (J. Inorg. Nucl. Chem., 38, 1175, 1976) and of Heumann and Schiefer (Z. Naturforsch., 36b, 566, 1981). The techniques employed involved liquid-liquid extraction and ion-exchange resins using specific complexing agents, such as crown ethers (dicyclohexano [18]crown-6) or cryptands (cryptand[2.2.2]).

The separation of the isotopes of rare earth metals by an ion-exchange resin (chromatography) in the liquid phase involving ion-exchange resins and an eluting solution comprising a ligand for the isotopes has also been provided. Thus, European Published Patent-A-173 484 provides such a technique for the separation of gadolinium isotopes using from 5 to 30, preferably from 20 to 30, columns comprising either an anion-exchange resin or a cation-exchange resin as stationary phase. In the first case, the eluant comprises ammonium nitrate in aqueous methanol and, in the second case, EDTA. Mention may similarly be made of J. Chen et al., Journal of Nuclear Science and Technology, 1992, 29 (11), 1086-1092, and I. M. Ismail et al., J. Chromato. A, 1998, 808, 185-191.

For reasons related essentially to the difficulties in controlling the elution of the isotope peaks, Published Patent WO-A-96/00124 has attempted to improve the separation of Gd isotopes on an ion-exchange resin. The method disclosed then requires a mobile phase preferably formed of an aqueous acid, preferably nitric acid. A similar method is provided by Published Patent WO-A-96/00123 for the separation of the erbium isotopes.

Other authors have provided a redox system by chemical exchange in liquid-liquid extraction systems with ligands of HDEHP or TBP type, for the separation of europium and cerium isotopes (W. Dembinski and T. Mioduski, Journal of Radioanalytical and Nuclear Chemistry, Letters, 1995, 199 (2), 159-171; W. Dembinski et al., Journal of Radioanalytical and Nuclear Chemistry, Articles, 1991, 149(1), 169-176).

French Published Patent 2 214 509 provides for the separation of the 44 and 40 isotopes of calcium by a liquid-liquid extraction process based on the use of crown ethers and of solvent of water-alcohol type or of chlorinated solvent.

The stakes are therefore high in the separation of isotopes. However, the various techniques have drawbacks, e.g. the complexity of the arrangements to be employed; the cost and the scale of the plants; the energy expenditure; the production of liquid or solid byproducts to a greater or lesser extent toxic; the use of solvents presents the problem of their separation and of their reprocessing, for the purpose of recycling them and of protecting the environment.

SUMMARY

It is therefore an object of the present invention to provide a process which allows efficient separation of isotopes from one another of the same element belonging to the category of alkaline earth metals, transition elements and heavy metals having an atomic mass of less than 209, in particular lanthanide metals.

Another object of the invention is to provide such a process which allows enrichment of an element in one or more advantageous isotopes.

Yet another object of the invention is to provide such a process which allows easy adjustment of the degree of separation or of enrichment.

Yet another object of the invention is to provide a process which is simple to implement, which does not require an excessively large plant and which is economic to use and to set up.

Yet another object of the invention is to provide such a process which allows limitation of the volumes of liquid and solid waste and not to generate toxic waste.

Yet another object of the invention is to provide such a process which is easy to implement and which limits energy expenditures.

Yet another object of the invention is to provide such a process which can operate easily batchwise or continuously.

Yet another object of the invention is to provide a process which allows high elution flow rates, in particular greater than those obtained in the other designs.

These objects, and others, are achieved by a process in which isotopes of the same element belonging to the alkaline earth metals, transition elements and heavy metals having an atomic mass of less than 209, in particular lanthanide metals, are separated in an aqueous medium by treating an aqueous medium comprising the isotopes using at least one organic ligand which is in the ionic state in the aqueous medium and which is designed to be able to complex preferentially with one or more of the isotopes present in the aqueous medium. The use of an appropriate separation arrangement then allows, on the one hand, retention of a retentate comprising the isotopes complexed with the ligand, which is reflected by an enriching of the retentate, with respect to the starting solution, in isotope(s) which complex preferentially and, on the other hand, to allow to pass or elute a permeate comprising the isotopes which have not complexed, which is reflected by a permeate or eluate enriched in isotopes which do not complex preferentially, namely isotopes which do not complex and/or isotopes which complex less strongly.

The metal to be treated is preferably in aqueous solution in the form of an isotope salt, in particular a nitrate, sulfate, carbonate or chloride.

The choice of the ligand falls on an organic ligand, which makes it possible to design and synthesize ligands according to precise specifications. In particular, the size of the ligand can be chosen so as to optimize the operation for separation between ligand-isotope complex and free isotopes as a function of the separation means used. Another parameter is the ionic charge of the ligand. The organic ligand may be chosen so as to have the same number of negative charges as the isotope in the ionic form has positive charges.

The invention is based on a surprising established fact: it is possible, with an appropriate ligand, to preferentially complex one or more isotopes of an element, at the expense of one or more others, this being achieved reproducibly, and then to separate the complexed isotopes from the noncomplexed isotopes.

The ligand is selected so as to make it possible to enrich either the permeate or the retentate in advantageous isotope, indeed even both when it is a matter of separating two advantageous isotopes.

The ligand may be a linear or cyclic, in particular linear, polyamino acid, which has, for example, the following formula (I):

$$(A^1)_a(R^1)_bC \left[ \begin{array}{c} N-(CR^3{}_2)_i \\ | \\ C(R^2)_c(A^2)_d \end{array} -\underset{O}{\overset{\|}{C}}-R^4-\underset{O}{\overset{\|}{C}}- \right]_p (R^5)_e \left[ \begin{array}{c} N-(CR^7{}_2)_h \\ | \\ C(R^6)_{f}(A^3)_g \end{array} \right]_q \underset{O}{\overset{\|}{C}}-R^8 \quad (I)$$

in which:
a=0 or 1 and b=2 or 3
c=2 or 3 and d=0 or 1
e=0 or 1
h=1, 2 or 3, preferably 1 or 2
i=1, 2 or 3, preferably 1 or 2
p=0 to 3, preferably 2
q=1 to 4, preferably 2 or 3
f=2 or 3
g=0 or 1
$A^1$, $A^2$ and $A^3$ are identical to or different from one another and correspond to a monovalent acid group for example selected from the group comprising: —COOR, —PO$_3$R'$_2$ and —SO$_3$R", where R, R' and R"=H or cation, in particular an alkaline cation, for example sodium; a cation which does not complex the ligand may be chosen;
the $R_1$ groups are identical to or different from one another and correspond to:
H,
$C_1$-$C_{10}$ alkyl or $$R^9R^{10}N\overset{O}{\overset{\|}{C}}—,$$

where a=0, b=1 and $R^9$ and $R^{10}$ identical or different and each corresponding to hydrogen or to a hydrophilic monovalent radical preferably selected from aminated and/or (poly)hydroxylated and/or alkoxylated and/or (poly)etherified hydrocarbonaceous residues, these residues may be of the (cyclo)alkyl, aralkyl, alkylaryl, (cyclo)alkenyl, aralkenyl, alkenylaryl or aryl type;

$R^9$ and $R^{10}$ more preferably still each corresponding to a $C_1$-$C_{10}$ hydroxyalkyl, a $C_1$-$C_{10}$ alkoxyl or a polyol, advantageously a hydrogenated saccharide;
the $R^2$ groups are identical to or different from one another,
the $R^3$ groups are identical to or different from one another,
the $R^6$ groups are identical to or different from one another,
the $R^7$ groups are identical to or different from one another,
$R^2$, $R^3$, $R^6$, $R^7$ are identical to or different from one another and correspond to H or to a $C_1$-$C_{10}$ alkyl;
the $R^4$ groups are identical to or different from one another and correspond to a hydrophilic divalent group for example selected from aminated and/or hydroxylated aromatic groups, aminated and/or hydroxylated aromatic and alkyl groups, aminated and/or hydroxylated aromatic and (cyclo)alkylene groups, or aminated and/or hydroxylated (cyclo)alkylene groups;
it being possible for this group to comprise alkoxy and/or (poly)ethers;
the divalent group $R^5$ representing an alkylene, preferably $CH_2$, or a group corresponding to the same definition as $R^4$; and/or
the group $R^8$ corresponding to a hydroxyl, to $A^4$ corresponding to the same definition as $A^1$, $A^2$, $A^3$, to hydrogen or to —NR$^9$R$^{10}$ with $R^9$, $R^{10}$ identical to or different from one another and representing a hydrophilic monovalent radical preferably selected from aminated and/or (poly)hydroxylated and/or alkoxylated and/or (poly)etherified hydrocarbonaceous residues, these residues preferably being of the (cyclo)alkyl aralkyl, alkylaryl, (cyclo)alkenyl, aralkenyl, alkenylaryl, aryl type;
$R^8$ being more preferably still a $C_1$-$C_{10}$ hydroxyalkyl, a $C_1$-$C_{10}$ alkoxyl or a polyol, advantageously a hydrogenated saccharide.

Any monovalent or divalent group or radical referred to in this formula (I) can be a linear or branched alkyl or alkenyl which may comprise, in its chain, one or more oxygen atoms in place of the carbon atoms (e.g. alkoxy or (poly)ether).

In this same formula (I), the term "aryl" group is understood to mean a group derived from an aromatic hydrocarbonaceous unit comprising one or more aromatic nuclei which may or may not be substituted by OH or alkyl groups or hydroxyalkyls by removal of one hydrogen atom from one of the carbons of the ring or by removal of one hydrogen atom from one of the carbons of an alkyl or hydroxyalkyl substituent. Mention may be made, by way of examples, of benzyl alcohol or hydroxyalkylphenol groups.

In this formula (I), the term "cycloalkylene" group is also understood to mean a divalent group derived from a hydrocarbocyclic which may or may not be substituted by alkyl or hydroxyalkyl chains by removal of one hydrogen atom from one carbon atom of the ring. Mention may be made, by way of example, of the cyclohexylene group.

The term "hydrocarbonaceous" is understood to mean, within the meaning of the invention, any group comprising in particular carbon atoms and hydrogen atoms.

When reference is made to $C_1$-$C_{10}$ alkyls, alkoxyls or alkenyls, it is a matter more specifically of $C_2$, $C_3$ and/or $C_4$ radicals.

Advantageously, the hydrophilic groups which may represent $R^9$ and $R^{10}$ are polyhydroxyalkyls, preferably hydrogenated saccharides, more preferably still a sorbitol residue, or polyether chains, preferably polyethylene glycol or polypropylene glycol.

Advantageously, this formula (I) encompasses known linear polyamino acids which are EDTA and DTPA (p=0, q=2 or 3, b=2, f=2, $A_1$=$A_3$=COOH, $R^1$=$R^6$=$R^7$=H, $R^5$=$CH_2$, $R^8$=OH, g=1,e=0,a=1,h=1 or 2).

According to one alternative form, the ligands/complexing agents may be cyclic polyamino acids, such as, for example, DOTAs, which are cyclic polyaminocarboxylates.

In an exemplary embodiment, the ligand/complexing agent is a product of formula (I.1):

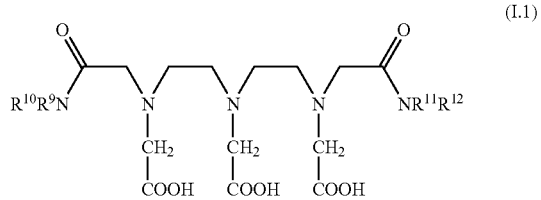

in which $R^9$, $R^{10}$, $R^{11}$, are identical to or different from one another and each represent a hydrophilic monovalent radical corresponding to the same definition as that given for $R^9$ and $R^{10}$, the ethanoyl, methoxyethyl and sorbitoyl radicals being more especially preferred.

A person skilled in the art can determine the values of the variables and can choose the substituents in order to design ligands suited to the isotopes to be treated.

On the basis of the information disclosed, a person skilled in the art is in a position to define appropriate ligands for the separation of such or such an isotope by resorting to simple experiments which are within the scope of his normal abilities and which can consist, for example, in repeating the process of the invention with a given ligand, in performing the separation and in analyzing the permeate and the retentate, as is described in particular in the examples.

In the first stage of this process, the water-soluble ligand according to the invention is added to the aqueous solution to be treated. The amount of ligand added may be such that it is less than one equivalent of ligand per atom of isotope to be separated. These ligands form complexes of 1:1 type.

According to a first form of the invention, the separation arrangement is a filtration membrane, preferably a nanofiltration membrane. The ligand and the membrane are chosen so that the molecular mass of the ligand-isotope complex is greater than the cutoff threshold of the membrane, so as to make possible a retention of the complexed ions which is as complete as possible.

To separate the isotopes, the aqueous solution to be treated is circulated in the vicinity of the nanofiltration membrane and a pressure difference is applied between the two opposite faces of the membrane, so as to collect a retentate enriched in isotope which complexes preferentially and a permeate depleted in this isotope. The pressure difference between the two opposite faces of the membrane can vary within a wide range but good results are obtained with a pressure difference ranging from 0.2 to 0.8 MPa.

The nanofiltration membranes capable of being used in the process of the invention must exhibit a cutoff threshold such that they allow the noncomplexed ions to pass and retain the ions complexed by the ligands of the invention. The cutoff threshold of a membrane with respect to a neutral solute can be defined as the minimum molar mass of a compound necessary in order to have a degree of retention of this compound at 90%.

According to the invention, the cutoff threshold appropriate for the membrane selected can be (in g/mol) from 100 to 5000, for example from 200 to 2000 and more preferably still from 500 to 1500. In practice, the cutoff threshold can, for example, be between 200 and 2000 g/mol.

These membranes can be organic, inorganic or organic/inorganic. They advantageously comprise or advantageously consist of polymers, such as polyaramides, sulfonated polysulfones, polybenzimidazolones, grafted or ungrafted poly(vinylidene fluoride)s, polyamides, cellulose esters, cellulose ethers or perfluorinated ionomers, the combinations of these polymers and the copolymers obtained from monomers of at least two of these polymers. For further details, a person skilled in the art may refer to Published Patent WO-A-92/06675, which discloses organic/inorganic nanofiltration membranes comprising an active layer of a polymer of the polysulfone, polybenzenimidazolone, grafted poly(vinylidene fluoride) and perfluorinated ionomer (Nafion®) type—cutoff threshold of 300 to 1000 g·mol$^{-1}$; or to French Published Patent FR 2 600 264, which discloses organic/inorganic membranes comprising a porous and organic support and a microporous membrane made of organic polymer, such as polysulfone, polyamide, cellulose ester and cellulose ether.

Mention may in particular be made, by way of examples of membranes, of the membranes sold by Osmonics under the names of Sepa MG-17, Sepa MW-15 and Sepa BQ-01, which have a permeability to doubly-distilled water of between 2 and 10 l·h$^{-1}$·m$^{-2}$·bar$^{-1}$ at 25° C.

Use may be made of the tangential filtration technique, which has the advantage of limiting the phenomenon of accumulation of the entities retained at the surface of the membrane and thus of making possible continuous operation.

Use may be made of filtration modules in the form of tubes or cylinders or of parallel plates or alternatively of membranes wound around a perforated tube or cylinder intended to collect the permeate. These modules can be arranged in series and/or in parallel, with optionally different membranes in some modules.

Mention may be made, by way of example, of the membrane sold by Millipore under the name Nanomax 50®, which is a spiral plan module, the membrane of which is formed of a polyester support, of a polysulfone intermediate layer and of a polyamide nanofiltering layer. Its characteristics are a high retention of polyvalent ions and of uncharged compounds with a molar mass M>350 g/mol and a high transmission of monovalent ions and of uncharged compounds with a molar mass M<100/mol.

The pH of the aqueous medium, the pressure difference applied, the rate of circulation of the retentate and the temperature are adjustable parameters.

The pH may be acidic and between 0 and 7, in order to avoid the precipitation of lanthanide hydroxides at high pH values.

It is possible to operate between 0 and 50° C. and advantageously at ambient temperature (25° C.) or in the vicinity of the latter, e.g. between 20 and 35° C. The pressure differences and rate of circulation of the retentate are above all set as a function of the desired flow rate and other characteristics of the membrane, e.g. its resistance to pressure. Simple tests allow the optimum conditions to be determined.

However, it may be specified that the pressure difference can vary between 0.2 and 1.5 MPa.

After their separation from the noncomplexed isotopes, the ligand/isotope complexes can be treated using appropriate decomplexing agent(s), so as to collect, on the one hand, the ligands and, on the other hand, the isotope or isotopes.

Thus, the complexed ions can, after filtration, be released or decomplexed, for example in a basic medium and by precipitation of their hydroxide or by passing through a specific ion-exchange resin. In the context of this stage, it is advantageous to provide, in accordance with the invention, for removal of the solvent, in this instance water, for example by evaporation, in order to make possible the recovery of the separated ions.

The equipment required for the implementation of the process according to the invention is relatively limited since a complexing reactor, a pump and at least one nanofiltration membrane are sufficient. By way of example, the basic plant can comprise a complexing reactor, a pump and a nanofiltration module, e.g. a tangential module, designed so that the retentate, after its passage in the vicinity of the membrane, is recycled upstream of the filtration module, such as in the complexing reactor. According to a particular form of the invention, the reactor can be fed continuously or semicontinuously with the ligand and the metal.

The nanofiltration can comprise several stages, in series and/or in parallel, so as to increase the degree of separation or of enrichment, permeate and/or retentate being subjected to the number of treatment and nanofiltration stages required by the object to be achieved.

Likewise, successive complexings/nanofiltrations with identical or different ligands can be performed, so as to make possible the separation of different isotopes in several stages.

Like the complexed isotopes, the decomplexed isotopes can again be treated and nanofiltered in accordance with the invention, this being performed at least once.

Nanofiltration has never until now been proposed for separating isotopes according to the invention, in particular lanthanide isotopes.

Another subject matter of the present invention is therefore the use of nanofiltration for separating the isotopes of an element belonging to the alkaline earth metals, transition metals and heavy metals having an atomic mass of less than 209, in particular lanthanide metals, these isotopes being in solution in an aqueous medium. The separation can take place in the absence of a ligand but, according to an exemplary form of the invention, the isotopes are treated with a ligand designed to complex preferentially with one or more of the isotopes of the element, after which nanofiltration is performed. The other characteristics and distinctive features mentioned above with respect to the ligands according to the invention apply to this other subject matter of the invention. The use of nanofiltration has numerous advantages in comparison with the prior techniques, in particular a low energy consumption, since it is possible in particular to operate at ambient temperature, good selectivity, a good elution flow rate, great flexibility of use, the possibility of operating continuously or semicontinuously and on a large scale, a low level of investment, high compactness of the separating stages, the absence of phase change, and the absence of organic solvent and of solid waste byproducts to be reprocessed.

In a second embodiment of the invention, the nanofiltration can be replaced by, or combined with, another separation arrangement, an ion-exchange resin or support of a specific type, carrying ligands as described above.

As in the first form, isotopes will bind preferentially to the ligands carried by the resin or support, while the isotopes which will not be complexed will pass through the resin or the support and will be found in the permeate. The elution stages subsequently make it possible to elute the isotopes which have complexed.

By definition, before an elution stage, the retentate is composed of the isotopes bonded to the ligands and therefore immobilized on the resin or the support. The permeate comprises the isotopes which have not been complexed to the ligands.

After an elution, the permeate corresponds by definition to the eluate.

Use may be made, in preparing these resins or supports, of polymer resins, in particular of styrene, polyester, polyamide, poly(alkene), polyether, polyimide or polyurethane type, or of graftable inorganic supports, such as silica, alumina and aluminosilicates. Preference is given to polystyrene-based resins and more particularly to copolymers based on styrene and on divinylbenzene. Reference may be made, by way of example, to example 8 below or to R. Garcia et al., 1998, Tetrahedron Letters, 39, 8651-8654, describing a resin based on a styrene derivative of DTPA (bis(diethanolamine)amide or of diethylenetriarninepentaacetic acid).

To prepare the resins according to the invention, it is possible in particular to polymerize the complexing monomer in the presence of one or more polymerizing and/or crosslinking agents (that is to say, the monomers which form the resin), preferably styrene and divinylbenzene, which results in the formation of covalent bonds between the support and the complexing part of the ligand. This type of polymer can also be obtained by grafting to this type of resin by formation of amide, ester or ether bonds between the ligand and the polymer matrix. With an inorganic support, the synthesis of resin is preferably based on a grafting method.

As in the case of nanofiltration, it is possible to use several stages, i.e. several chromatography columns comprising a resin or a support in accordance with the invention, it being possible for these columns to be arranged in series and/or in parallel, so as to retreat the retentate after elution and/or the permeate for the purpose of the separation of the desired isotopes and their enrichment according to the specifications. Likewise, during the same process, it is possible to employ different resin (or support)-ligand pairs so as to optimize the separation of the isotopes, in particular when several isotopes are desired from those in the starting mixture.

Nanofiltration and passage through a resin or support can advantageously be combined. In this case, it is preferable for the nanofiltration stage or stages to precede the stage or stages through the resin or support.

The elution of the complexed isotopes can be performed by various aqueous solutions, in particular an acid solution, a solution of cations or a solution comprising a ligand capable of detaching the isotopes immobilized on the resin, such as EDTA, DTPA or their derivatives, in particular those defined by the formula (I).

A further subject matter of the invention is the use of a, polymeric resin or of an inorganic support carrying a ligand according to the invention for the separation of isotopes of an element belonging to the alkaline earth metals, transition elements and heavy metals having an atomic mass of less than 209, in particular lanthanide metals. The other characteristics and distinctive features described above with regard to the separation method apply to this other subject matter of the invention.

The present invention also relates to a novel compound, the N-acetamidostyreneethylenediaminetriacetic acid, the formula of which and a process for the preparation of which are shown in example 7.

Another subject matter of the invention is the use of this compound as a ligand in the isotopic separation process in accordance with the invention. Another subject matter of the invention is the use of this compound as ligand attached to an inorganic resin or support in accordance with the invention for preparation of an ion-exchange resin or support according to the invention. Another subject matter of the invention is such resins or supports carrying this ligand. A very particular subject matter of the invention is a styrene divinylbenzene-N-acetamidostyreneethylenediaminetriacetic acid polymer such as, for example, described and produced according to example 8. The invention also relates to the use of such a resin for the isotopic separation in accordance with the invention.

DETAILED DESCRIPTION

The invention will now be described in more detail and using embodiments taken as nonlimiting examples.

EXAMPLE 1

Synthesis of DTPA bis(diethanolamine)amide (1)

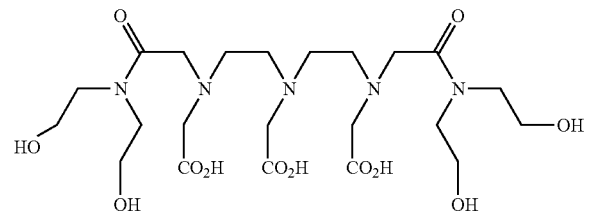

10 grams of DTPA anhydride (27.98 mmol) are dissolved in 150 ml of anhydrous DMF (DiMethylFormamide) at 80° C. under an inert atmosphere (argon) in a 500 ml three-necked flask. 17 grams of diethanolamine (167.9 mmol) in 50 ml of DMF are added dropwise and the reaction medium is kept stirred for 48 hours. The oily residue obtained is separated from the solvent by settling. After dissolving this residue in the minimum amount of water, 800 ml of acetone are added and the viscous precipitate is triturated, isolated from the solvent by separation by settling, and purified on a column of Amberlite IR-120 (Fluka) ion-exchange resin by elution with distilled water. After evaporation and drying under vacuum, 7.98 g of product (1) are obtained in the form of a white powder (yield of 50%).

$^1$H NMR ($D_2O$): 3.1 (t, J=6.25, 4H), 3.48-3.52 (t+s, 10H), 3.59 (t, J=6.2, 4H), 3.76 (t, J=5.2, 8H), 3.91 (s, 4H), 4.49 (s, 4H). $^{13}$C NMR ($D_2O$): 50.59, 55.88, 56.62, 58.84, 59.95 ($CH_2CO_2H$ and $NCH_2CH_2N$), 51.75, 52.14, 60.85, 61.2 ($N(CH_2CH_2OH)_2$), 169.02, 172.6, 176.8 ($CO_2H$ and CO). ES-MS: ES$^-$: 566.3 ([M–H]$^-$), 282.7 ([M-2H]$^{2-}$/2).

EXAMPLE 2

Isotopic Separation of Gd by Nanofiltration-complexing with DTPA bis(diethanolamine)amide (1)

The plant comprises a complexing reactor, a pump and then a flat filtration module equipped with the Sepa MG-17 membrane (with a filtering area S=0.015 m$^2$). The Sepa MG-17 flat membrane exhibits a permeability to doubly-distilled water of 2.5 l·h$^{-1}$·m$^{-2}$·bar$^{-1}$ at 25° C. The retentate outlet is connected to the complexing reactor. This plant will be used for all the nanofiltration examples.

In this example, an aqueous solution with a volume of 1 liter, comprising 10 mmol/l of gadolinium (Gd) in the form of gadolinium nitrate hexahydrate, is treated. A complexing agent composed of the complexing agent (1) of example 1 is added to the aqueous solution to be treated.

The isotopic separation of Gd is carried out under the following conditions:
transmembrane pressure $\Delta P$=0.6 MPa,
temperature=20° C.,
retentate flow rate=80 l/h,
pH=3.8.

Complexing agent (1) is added to a level of 9 mmol/l (i.e. 90% of ligand with respect to the gadolinium). 700 ml of the solution are filtered. At the end of the experiment, a volume of retentate of 300 ml and a volume of permeate of 700 ml are obtained. A sample of permeate and a sample of retentate are withdrawn. The final retentate comprises 1260 mg/l of Gd, the final permeate comprises 136 mg/l thereof (i.e. a mean degree of retention of 89% during the filtration). The analysis of the two samples by ICP-MS (Inductively Coupled Plasma-Mass Spectroscopy) reveals the following results:

mean value of the ratio $^{160}$Gd/$^{155}$Gd in the retentate: 1.5086±0.0016 mean value of the ratio $^{160}$Gd/$^{155}$Gd in the permeate: 1.5128±0.0011, i.e., between the permeate and the retentate, an enrichment factor of 1.0028±0.0018 between the $^{160}$Gd and $^{155}$Gd isotopes. The permeate has been enriched in $^{160}$Gd.

EXAMPLE 3

Isotopic Separation of Nd by Nanofiltration-complexing with DTPA bis(diethanolamine)amide (1)

In this example, an aqueous solution with a volume of 500 ml, comprising 5 mmol/l of neodymium (Nd) in the form of neodymium nitrate hexahydrate, is treated. A plant identical to that of example 1 is used. A complexing agent composed of the complexing agent (1) of example 1 is added to the aqueous solution to be treated.

The isotopic separation of Nd is carried out under the following conditions:
transmembrane pressure $\Delta P$=0.6 MPa,
temperature=20° C.,
retentate flow rate=80 l/h,
pH=3.8.

Complexing agent (1) is added to a level of 4.5 mmol/l (i.e. 90% of ligand with respect to the neodymium). The solution is filtered while recycling both the retentate and permeate circuits. At chemical equilibrium, a sample of permeate and a sample of retentate are withdrawn. The retentate comprises 613 mg/l of Nd, the permeate comprises 84 mg/l thereof (i.e. an instantaneous degree of retention of 87%). The analysis of the two samples by ICP-MS reveals the following results:

mean value of the ratio $^{150}$Nd/$^{142}$Nd in the permeate: 0.22233±0.00034 mean value of the ratio $^{150}$Nd/$^{142}$Nd in the retentate: 0.22187±0.00040, i.e., between the permeate and the retentate, an enrichment factor of 1.0021±0.0006 between the $^{150}$Nd and $^{142}$Nd isotopes. The permeate has been enriched in $^{150}$Nd.

EXAMPLE 4

Synthesis of the Copolymer
DTPA-4,4"-methylenedianiline (2)

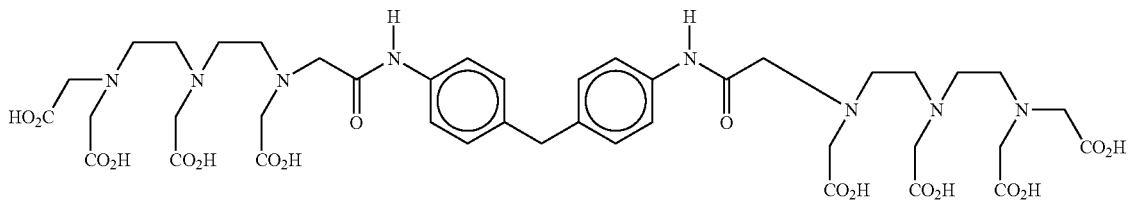

1.179 grams of DTPA dianhydride (3.3 mmol) are dissolved in 120 ml of anhydrous DMF at 50° C. under an inert atmosphere (argon) in a 250 ml three-necked flask. 595 milligrams of 4,4'-methylenedianiline (3 mmol) in 45 ml of anhydrous DMF are added dropwise and the reaction medium is kept stirred for 4 hours at 50° C. The reaction mixture is run onto 500 ml of diethyl ether. The precipitate is filtered off and washed with 3 times 100 ml of diethyl ether. After drying under vacuum, 1.28 g of product (2) are obtained in the form of a white powder (yield of 72%).

$^1$H NMR (D$_2$O): 7.17 (broad s, 2H), 6.76 (m, 2H), 3.3-2.1 (m, 14H). Calculation of the degree of polymerization by $^1$H NMR: i.e.:
R=area aromatic CH/area aliphatic CH$_2$=0.296
n=−18R/(20R−8)=2.57

EXAMPLE 5

Synthesis of DTPA bis(di(2-methoxyethyl-amide)(3)

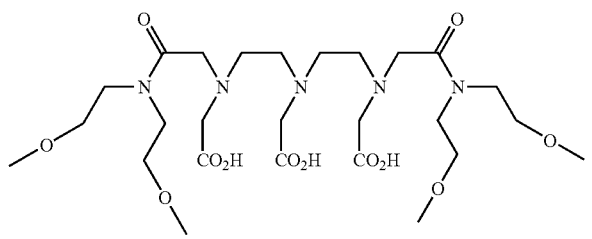

12.4 ml of bis(2-methoxyethyl)amine (0.084 mol), dissolved in 40 ml of anhydrous DMF, are added dropwise to 5 grams of DTPA anhydride (0.014 mol), dissolved in 80 ml of anhydrous DMF, under argon at 80° C. The reaction medium is kept stirred for 24 hours. After concentrating and addition of diethyl ether, the oily precipitate is separated from the solvents by settling. This residue is dissolved in the minimum amount of CHCl$_3$ and reprecipitated from Et$_2$O. After drying under vacuum, a hygroscopic foam (3) is obtained (6.43 g, yield of 74%), used without additional purification.

$^1$H NMR (D$_2$O+NaOD): 2.50 (t, 4H), 2.52 (t, 4H), 2.98 (s, 2H), 3.11 (s, 4H), 3.31 (s, 6H), 3.32 (s, 6H), 3.51 (s, 4H), 3.53-3.56 (m, 16H). $^{13}$C NMR (D$_2$O): 45.94, 47.03, 47.81, 49.75, 53.69, 56.29, 57.78, 67.16, 69.56, 69.69 (CH$_2$); 58.63, 59.07 (OCH$_3$); 166.9, 170.5, 175.7 (CO$_2$H and CO). ES-MS: ES$^-$: 622.1 ([M−H]$^-$), ES$^+$: 624.3 ([M+H]$^+$), 646.2 ([M+Na]$^+$).

EXAMPLE 6

Synthesis of DTPA bis(1-deoxy-1-amidosorbitol)

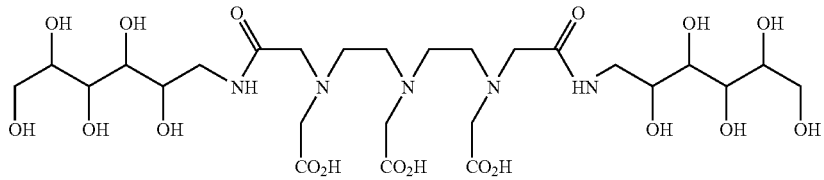

5 grams of DTPA anhydride (0.014 mol) are dissolved in 100 ml of anhydrous DMF at 70° C. under argon in a 500 ml three-necked flask. 5.32 grams of 1-deoxy-1-aminosorbitol (0.029 mol), dissolved in 40 ml of DMSO, are added dropwise and the reaction medium is kept stirred for 24 hours. The viscous residue resulting from the reaction is separated from the solvents after separation by settling. It is subsequently dissolved in the minimum amount of water and reprecipitated by addition of acetone. The operation is repeated a second time and the residual oil is separated by settling and dried under vacuum to give a slightly tinged white foam (4) (6.66 g, yield of 66%).

$^{13}$C NMR (D$_2$O): 42.17, 47.14, 49.61, 53.41, 56.73, 57.48, 63.16 (CH$_2$); 69.44, 71.08, 71.18, 71.38 (CH); 171.0, 178.86 (CO$_2$H and CO). ES-MS: ES$^+$: 741.2 ([M+Na]$^+$).

EXAMPLE 7

Synthesis of N-acetamidostyreneethylenediaminetriacetic acid (5)

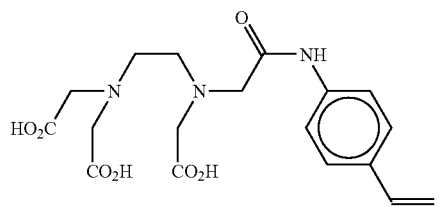

5 grams of EDTA dianhydride (19.5 mmol) are dissolved in 120 ml of anhydrous DMF at 70° C. under an inert atmosphere (argon) in a 250 ml three-necked flask. 2.09 grams of 4-vinylaniline (17.57 mmol) in 20 ml of anhydrous DNF are added dropwise and the reaction medium is kept stirred for 24 hours. The solution is concentrated and the oily residue obtained is triturated in ethyl ether. A pink solid is obtained after filtration. This solid is suspended in acetone and then filtered off The solid is taken up in deionized water, triturated and then filtered off. After drying under vacuum, 4.2 grams of product (5) are obtained in the form of a pale-pink powder.

$^1$H NMR (d$^6$-DMSO)(ppm): 2.8 (s, 4H), 3.48 (m, 8H), 5.17 (d, 1H), 5.73 (d, 1H), 6.67 (dd, 1H), 7.42 (d, 2H), 7.62 (d, 2H). $^{13}$C NMR (DMSO d$^6$)(ppm): 51.3, 51.4, 52.0, 54.55, 55.1, 55.3, 58.0, 112.7, 119, 126.5, 132.2, 136.1, 138.5, 169.7, 172.2, 172.9.

EXAMPLE 8

Synthesis of the styrene-divinylbenzene-N-acetamidostyreneethylenediaminetriacetic acid polymer (6)

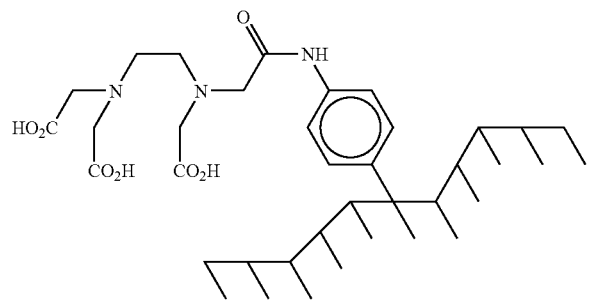

6 grams of N-acetamidostyreneethylenediaminetriacetic acid (15.2 mmol) are dissolved in 40 ml of MeOH in a glass reactor under an inert atmosphere. 3.89 grams of ground sodium nitrate (45.7 mmol) are added. This solution is placed in the water bath of an ultrasonic tank and subjected to ultrasound for 15 minutes. 16.5 ml of styrene, 1.49 ml of divinylbenzene and 50 mg of AIBN (azoisobutyronitrile) are added. The solution is stirred and heated for 72 hours at 65° C. The solid obtained is washed with MeOH, then suspended in a flask comprising 250 ml of MeOH and stirred for 24 hours. The solid is filtered off, then washed 5 times with an aqueous hydrochloric acid solution (1N), then 5 times with an aqueous sodium hydroxide solution (0.1N) and finally with deionized water to a pH of 5-6. This resin is dried in a desiccator comprising P$_2$O$_5$. 15.96 grams of polymer are obtained (yield of 72%).

Elemental analysis: found % C: 71.61; % H: 6.84; % N: 3.65.

EXAMPLE 9

Separation of the Gadolinium Isotopes in Solid-liquid Extraction

A suspension of 5.5 grams of sieved styrene-divinylbenzene-(N-acetamidostyrene) polymer (6) (particle size from 108 to 300 µm) in an aqueous sodium nitrate solution (C=1×10$^{-2}$ mol·l$^{-1}$) is introduced into a chromatography column for high pressure liquid chromatography (HPLC) made of stainless steel, the lower end of which is connected to a pump. The column is subjected to vibrations in order to tamp down the polymer and avoid the formation of air bubbles. Once filled, the column is hermetically sealed and then mounted in series with a pump used in high pressure liquid chromatography. A sodium nitrate solution (C=1×10$^{-2}$ mol·l$^{-1}$) is eluted in order to confirm that the pressure remains constant and in order to adjust the flow rate (flow rate=0.2 ml·min$^{-1}$, pressure=12 bar). Finally, 1 l of an aqueous gadolinium nitrate solution is eluted (C=1×10$^{-2}$ mol/l). The solution is then fractionated into samples with a size of 11 ml at the column outlet. These different fractions are quantitatively determined in ICP-AES in order to determine the sodium and gadolinium content of each sample. The analysis of three samples (starting solution and two solutions corresponding to added volumes of 220 ml (S$_{20}$) and 275 ml (S$_{25}$) of Gd(NO$_3$)$_3$·6H$_2$O) by ICP-MS reveals the following results:

mean value of the ratio $^{160}$Gd/$^{155}$Gd in the starting solution: 1.52505±0.00107 mean value of the ratio $^{160}$Gd/$^{155}$Gd in the solution S$_{20}$: 1.51297±0.00417 mean value of the ratio $^{160}$Gd/$^{155}$Gd in the solution S$_{25}$: 1.51883±0.00222, i.e. enrichment factors for S$_{starting}$/S$_{20}$=1.0080±0.0035 between the isotopes $^{160}$Gd and $^{155}$Gd and S$_{starting}$/S$_{25}$=1.0041±0.0022 between the isotopes $^{160}$Gd and $^{155}$Gd. The light isotopes emerge first from the column (selective retention of the heavy isotopes in the column).

It should be clearly understood that the invention defined by the appended claims is not limited to the specific embodiments indicated in the above description but encompasses the alternative forms which depart neither from the scope nor from the spirit of the present invention.

What is claimed is:

1. A process for separating, in an aqueous medium, isotopes of a same element selected from the group consisting of alkaline earth metals, transition elements and heavy metals having an atomic mass of less than 209, the process comprising:

treating the aqueous medium comprising the isotopes with a ligand designed to complex with at least one of the isotopes of the element; and nanofiltering the treated aqueous medium to separate the isotopes.

2. The process according to claim 1, wherein an amount of ligand employed is one of less than 1 equivalent of ligand per atom of isotope and of the isotopes to be complexed.

3. The process according to claim 1, wherein the ligand is chosen so as to have a same number of negative charges as the isotope in the ionic form has of positive charges.

4. The process according to claim 1, wherein the ligand has one of a linear and cyclic polyamino acid as defined by

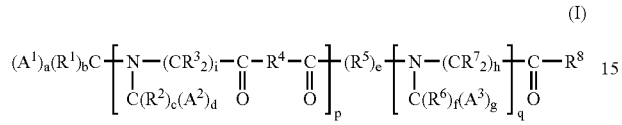
(I)

in which:
a=0 or 1 and b=2 or 3
c=2 or 3 and d=1 or 1
p=0 to 3,
e=0 or 1
h=1, 2 or 3
i=1, 2 or 3
q=1 to 4
f=2 or 3
g=0 or 1
the $A^1, A^2, A^3$ are one of identical to and different from one another and correspond to a monovalent acid group,
the $R^1$ groups are one of identical to and different from one another and correspond to:
H,
$C_1$-$C_{10}$ alkyl; or one $R^1$ may be

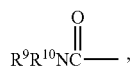

where a=0, and the $R^9$, $R^{10}$ groups are one of identical to and different from one another, and each corresponding to one of hydrogen and a hydrophilic monovalent radical selected from at least one of aminated and (poly)hydroxylated and alkoxylated and (poly)etherified hydrocarbonaceous residues,
the $R^2$ groups are one of identical to and different from one another,
the $R^3$ groups are one of identical to and different from one another,
the $R^6$ groups are one of identical to and different from one another,
the $R^7$ groups are one of identical to and different from one another, wherein the $R^2$, $R^3$, $R^6$, $R^7$ are one of identical to and different from one another and correspond to one of H and to a $C_1$-$C_{10}$ alkyl;

the $R^4$ groups are one of identical to and different from one another and correspond to a hydrophilic divalent group selected from the group consisting of aminated aromatic groups, hydroxylated aromatic groups, aminated and hydroxylated aromatic groups, aminated aromatic and alkyl groups, hydroxylated aromatic and alkyl groups, aminated and hydroxylated aromatic and alkyl groups, aminated aromatic and (cyclo)alkylene groups, hydroxylated aromatic and (cyclo)alkylene groups, aminated and hydroxylated aromatic and (cyclo)alkylene groups, aminated (cyclo)alkylene groups, hydroxylated (cyclo)alkylene groups, and aminated and hydroxylated (cyclo)alkylene groups;
the divalent group $R^5$ representing one of an alkylene, and a group corresponding to a same definition as $R^4$; and
the group $R^8$ corresponding to a hydroxyl, to $A^4$ corresponding to a same definition as one of the $A^1$, $A^2$ and $A^3$, to hydrogen, or to —$NR^9R^{10}$ with $R^9$ and $R^{10}$ one of identical to and different from one another and representing a hydrophilic monovalent radical selected from at least one of aminated and (poly)hydroxylated and alkoxylated and (poly)etherified hydrocarbonaceous residues.

5. The process according to claim 4, wherein at least one of the hydrophilic groups $R^9$ and $R^{10}$ are polyhydroxyalkyls.

6. The process according to claim 5, wherein at least one of the $R^9$ and $R^{10}$ are hydrogenated saccharides.

7. The process according to claim 5, wherein at least one of the $R^9$ and $R^{10}$ are polyether chains.

8. The process according to claim 4 wherein the ligand is a compound of formula:

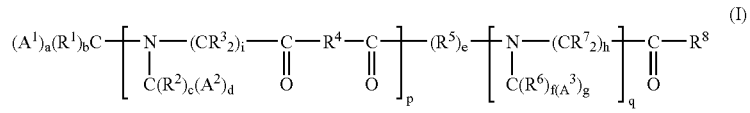
(I)

in which the $R^9$, $R^{10}$, $R^{11}$, $R^{12}$ are one of identical to and different from one another and each represent a hydrophilic monovalent radical corresponding to same definition as that given for the $R^9$, $R^{10}$.

9. The process according to 3, wherein at least one of the $R^9$, $R^{10}$, $R^{11}$ and $R^{12}$ are chosen from ethanoyl, methoxyethyl and sorbitoyl radicals.

10. The process according to claim 4, wherein at least one of $R^9$ and $R^{10}$ are residues selected from the group consisting of (cyclo)alkyl, aralkyl, alkylaryl, (cyclo)alkenyl, aralkenyl, alkenylaryl and aryl.

11. The process according to claim 10, wherein the alkyl, alkoxyl and alkenyl groups are at least one of the $C_2$, $C_3$ and $C_4$ groups.

12. The process according to claim 10 wherein $R^8$ is selected from the group consisting of a $C_1$-$C_{10}$ hydroxyalkyl, a $C_1$-$C_{10}$ alkoxyl and a polyol.

13. The process according to claim 10, wherein $R^4$ comprises at least one of alkoxy and (poly)ethers.

14. The process according to claim 10, wherein the monovalent acid group is selected from the group consisting of —COOR, —$PO_3R'_2$ and —$SO_3R''$, wherein R, R' and R'' are a hydrogen or a cation.

15. The process according to claim 4, wherein the monovalent acid group is selected from the group consisting of —COOR, —$PO_3R'_2$ and —$SO_3R''$, wherein R, R' and R'' are a hydrogen or a cation.

16. The process according to claim 15, wherein the cation is sodium.

17. The process according to claim 15, wherein the cation does not complex the ligand.

18. The process according to claim 4, wherein $R^9$ and $R^{10}$ are selected from the group consisting of a $C_1$-$C_{10}$ hydroxyalkyl, a $C_1$-$C_{10}$ alkoxyl and a polyol.

19. The process according to claim 18, wherein $R^8$ is selected from the group consisting of a $C_1$-$C_{10}$ hydroxyalkyl, a $C_1$-$C_{10}$ alkoxyl and a polyol.

20. The process according to claim 18, wherein $R^4$ comprises at least one of alkoxy and (poly)ethers.

21. The process according to claim 18, wherein the monovalent acid group is selected from the group consisting of —COOR, —$PO_3R'_2$ and —$SO_3R''$, wherein R, R' and R" are a hydrogen or a cation.

22. The process according to claim 21, wherein the cation does not complex the ligand.

23. The process according to claim 4, wherein $R^8$ is selected from the group consisting of a $C_1$-$C_{10}$ hydroxyalkyl, a $C_1$-$C_{10}$ alkoxyl and a polyol.

24. The process according to claim 23, wherein $R^4$ comprises at least one of alkoxy and (poly)ethers.

25. The process according to claim 23, wherein the monovalent acid group is selected from the group consisting of —COOR, —$PO_3R'_2$ and —$SO_3R''$, wherein R, R' and R" are a hydrogen or a cation.

26. The process according to claim 4, wherein $R^4$ comprises at least one of alkoxy and (poly)ethers.

27. The process according to claim 26, wherein the monovalent acid group is selected from the group consisting of —COOR, —$PO_3R'_2$ and —$SO_3R''$, wherein R, R' and R" are a hydrogen or a cation.

28. The process according to claim 1, wherein the separated isotopes are lanthanide isotopes.

29. The process according to claim 1, wherein the separated isotopes are selected from the group consisting of gadolinium isotopes, erbium isotopes and neodymium isotopes.

30. The process according to claim 1, wherein the nanofiltering is performed through a tangential nanofiltration.

31. The process according to claim 1, wherein the separated isotopes are gadolinium isotopes.

32. The process according to claim 1, wherein the separated isotopes are erbium isotopes.

33. The process according to claim 1, wherein the separated isotopes are neodymium isotopes.

* * * * *